(12) United States Patent
Bindra et al.

(10) Patent No.: US 8,308,043 B2
(45) Date of Patent: Nov. 13, 2012

(54) RECOGNITION OF INTERCHANGEABLE COMPONENT OF A DEVICE

(75) Inventors: Manjit Singh Bindra, Karnataka (IN); Prabhu Ramlingam, Karnataka (IN); Adam J. Ross, Prospect, CT (US); Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 285 days.

(21) Appl. No.: 12/762,557

(22) Filed: Apr. 19, 2010

(65) Prior Publication Data

US 2010/0294828 A1    Nov. 25, 2010

Related U.S. Application Data

(60) Provisional application No. 61/179,397, filed on May 19, 2009.

(51) Int. Cl.
  *A61B 17/068* (2006.01)
(52) U.S. Cl. ............... 227/176.1; 227/179.1; 227/180.1
(58) Field of Classification Search ............... 227/176.1, 227/179.1, 180.1; 606/1, 151, 219
  See application file for complete search history.

(56) References Cited

U.S. PATENT DOCUMENTS

| | | |
|---|---|---|
| 5,395,033 A | 3/1995 | Byrne et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,562,239 A | 10/1996 | Boiarski et al. |
| 5,836,867 A * | 11/1998 | Speier et al. .................. 600/112 |
| 7,055,730 B2 | 6/2006 | Ehrenfels et al. |
| 7,159,750 B2 | 1/2007 | Racenet et al. |
| 7,301,332 B2 | 11/2007 | Govari et al. |
| 7,303,528 B2 | 12/2007 | Couvillon, Jr. |
| 7,588,546 B2 * | 9/2009 | de Andrade ................... 600/567 |
| 2003/0069475 A1 | 4/2003 | Banik et al. |
| 2004/0267297 A1 * | 12/2004 | Malackowski ................ 606/167 |
| 2005/0131390 A1 * | 6/2005 | Heinrich et al. ................... 606/1 |
| 2007/0023476 A1 | 2/2007 | Whitman et al. |
| 2007/0175956 A1 | 8/2007 | Swayze et al. |
| 2008/0164296 A1 | 7/2008 | Shelton et al. |
| 2008/0179374 A1 | 7/2008 | Beardsley et al. |
| 2008/0185419 A1 * | 8/2008 | Smith et al. ................. 227/179.1 |
| 2008/0251568 A1 | 10/2008 | Zemlok et al. |
| 2008/0251569 A1 | 10/2008 | Smith et al. |
| 2008/0255418 A1 | 10/2008 | Zemlok et al. |

* cited by examiner

*Primary Examiner* — Lindsay Low
*Assistant Examiner* — Nathaniel Chukwurah (57) ABSTRACT

A device and a method are provided for determining a characteristic of an interchangeable component of a surgical instrument. An electrically conductive material having a measurable strength measurable by a hall effect sensor is coupled to the component. In another embodiment, a plurality of conductive materials are arranged to form a binary code representing a corresponding of the interchangeable component. The number and/or strength of the magnets measurable by the sensors may be dynamically altered such that the status of the surgical instrument is determinable.

9 Claims, 7 Drawing Sheets

RECOGNITION OF INTERCHANGEABLE COMPONENT OF A DEVICE

CROSS-REFERENCE TO RELATED APPLICATIONS

This application claims priority to, and the benefits of, U.S. Provisional Application No. 61/179,397, filed on May 19, 2009, the entire contents of which are hereby incorporated by reference.

BACKGROUND

1. Technical Field

The present disclosure relates generally to a device and a method for recognizing characteristics, e.g., type and/or status, of an interchangeable part of a surgical instrument. In particular, the present disclosure relates to the recognition of a single use loading unit ("SULU") such as a staple cartridge of a surgical stapling device.

2. Background of Related Art

During a surgical procedure, it is essential that a surgeon be able to readily and reliably ascertain whether an instrument selected for the procedure is appropriate for its intended use. It is common for a surgical instrument to include interchangeable components that may be replaced with different components better suited for the particular procedure. Alternatively, the component may require replacement once used.

Many surgical instruments include removable or interchangeable components. Prior to using such a surgical instrument, the identification of the particular components coupled or placed within the surgical instrument is essential. Examples of surgical instruments that include a removable SULU include U.S. Pat. Nos. 7,055,730 and 7,159,750, the contents of which are hereby incorporated by reference in their entireties. In particular, U.S. Pat. No. 7,055,730 discloses a surgical fastener applying apparatus including a SULU and includes a cartridge half-section and an anvil half-section, with the cartridge and anvil half-sections being relatively movable from an unclamped position to a fully clamped position. U.S. Pat. No. 7,159,150 discloses a surgical stapling device that is designed for use with a SULU, which is attachable to an elongated body portion of the device.

The type and/or status of the SULU that is operatively coupled with a particular surgical instrument is essential to ascertain prior to using the instrument. However, the identity and status of a SULU is complicated by the fact that SULUs may differ in size and configuration and in the surgical fasteners housed therein. Moreover, a SULU's type and/or status may not be readily apparent from visual inspection since the SULU may not have distinguishing external characteristics or may be obscured from view.

SUMMARY

The present disclosure relates to a device and a method for identifying a characteristic of an interchangeable component of a surgical instrument.

A surgical apparatus may include a receiving section including one or more sensors. An interchangeable component (e.g., a staple cartridge or an end effector) of the surgical instrument is adapted and configured to be removably coupled to a receiving section of the surgical apparatus (e.g., a cartridge receiving section or a distal end of an elongated shaft). The interchangeable component of a surgical instrument having a characteristic to be identified includes at least one magnet coupled to the interchangeable component, the magnet having a strength that is measured by a sensor, e.g., a hall-effect sensor. The magnet has a magnetic strength corresponding to a characteristic of the interchangeable component to be identified. A plurality of the at least one magnets are arranged to represent a binary code corresponding to a characteristic of the interchangeable component to be determined. In particular, the surgical apparatus may include a given number of sensors that is adapted and configured to detect the presence or absence of a particular magnet. The arrangement of the present magnets represents a binary code that corresponds to a certain characteristic. For example, in the case of an interchangeable staple cartridge, the characteristic may be the size or dimensions of the staples contained within the staple cartridge.

An electrically conductive element, e.g., a magnet having a strength corresponding to a particular characteristic to be identified may be coupled to the interchangeable component. For example, a magnet having a 1,000 gauss power rating may correspond with a SULU of a surgical stapling instrument containing absorbable copolymer staples. In another embodiment, a plurality of electrically conductive elements may be arranged to represent a binary code to indicate the characteristic to be identified. A controller is able to determine the type and/or status of the interchangeable component from the inputted corresponding measured characteristic.

In an embodiment, the determination of the status of the SULU may be achieved by dynamically altering the strength, arrangement, or detectability of the magnets, e.g., by moving or covering the magnets in response to status changes of the SULU such that the number or strength of magnets as measured by the sensor may be dynamically altered. In so doing, such status indicators as the number of staples remaining in the SULU may be determined.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the presently disclosed device and method for identifying a characteristic of a component of a surgical instrument are described in detail with reference to the drawings, in which like reference numerals designate identical or corresponding elements in each of the several views.

Figure 1:
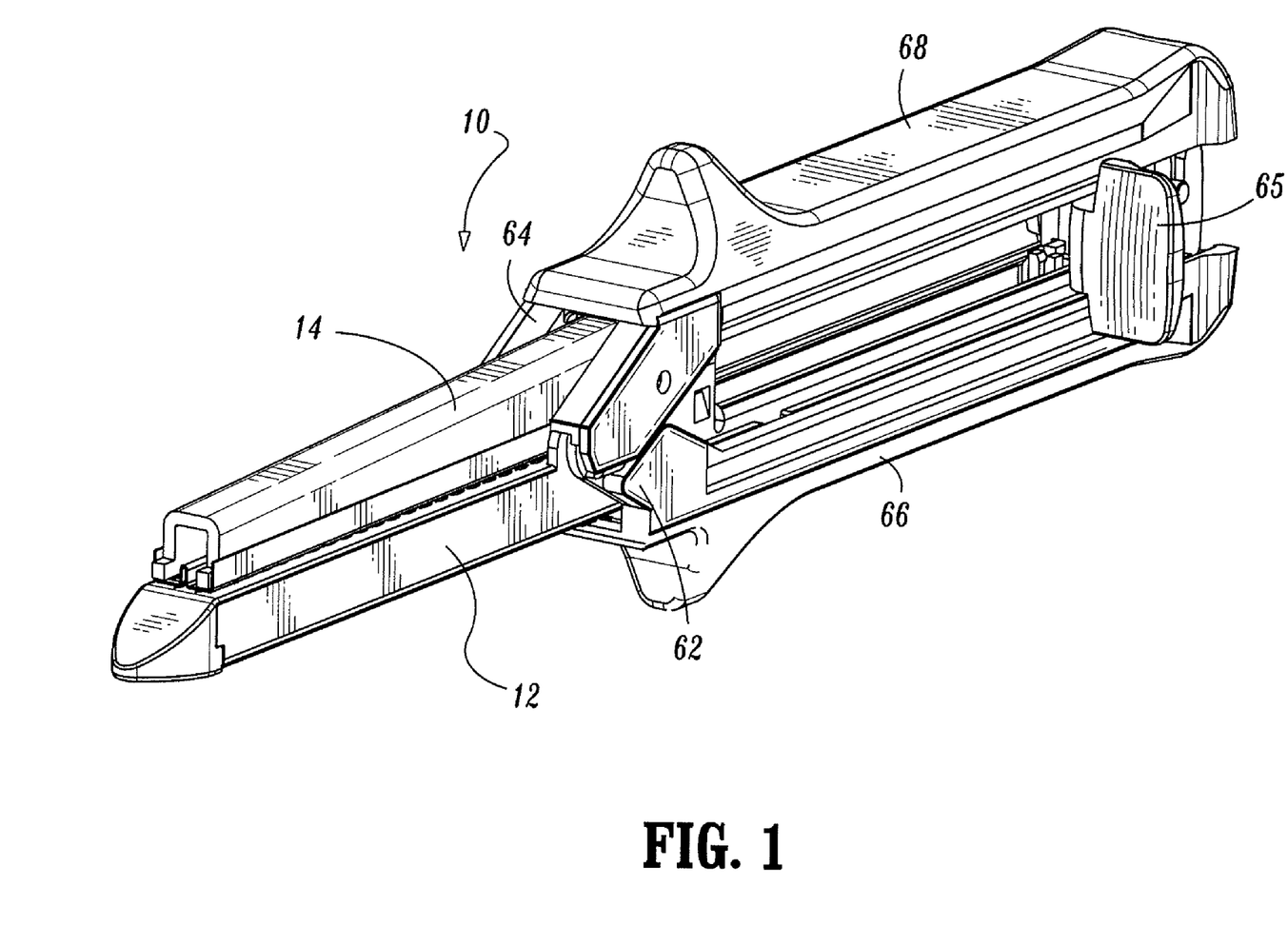
FIG. 1 is a perspective view of a surgical fastener apparatus including a staple cartridge assembly.

A surgical stapling device 10 will now be described with reference to FIGS. 1-3. The surgical stapling device 10 is adapted and configured to apply a plurality of adjacent rows of staples to body tissue clamped between a cartridge receiving section 12 and an anvil section 14. The surgical stapling device 10 is provided with dual selectable clamping levers 62, 64 and a slidably mounted firing lever 65. Clamping levers 62, 64 provide the user with the option of opening the stapling device 10 from either half-section 12, 14. A pair of ergonomic contoured handles 66, 68 is secured to the clamping levers 63, 64, respectively. Additionally, firing lever 65 provides the user with the ability to fire the surgical stapling device 10 from either the left or right side.

A SULU 16 includes a cartridge body 18 is provided with several molded surfaces to facilitate mounting and alignment of SULU 16 with respect to cartridge half-section 12 of surgical stapling device 10. Such alignment facilitating surfaces may be formed at any suitable location on the various components of cartridge body 18 to correspond with complementary surfaces on cartridge half-section 12. For example, locating/alignment feature surfaces 18a may be formed extending downwardly on either side of SULU 16 near the proximal end thereof and molded surfaces 18b may be formed on either side of cartridge body 18 near the distal end thereof.

When SULU 16 is properly installed on surgical stapling device 10, surfaces 18a seat in a pair of notches 38, 50 formed in cartridge half-section 12. A rocker 52 is further provided with a, downwardly extending blocking surface 52e which is in vertical alignment with an opening formed through the bottom surface of cam bar channel 40 when cam bar channel 40 is in its proximal-most position. The rocker 52 may be biased by way of a spring 56 toward a locked-out position wherein blocking surface 52e extends through opening 40a, such that cam bar channel 40 is inhibited from distal longitudinal movement. Seen in FIG. 3, the SULU 16 may be operatively engaged with a beam 58. In versions of a surgical stapling device 10 using shorter SULUs 16, beam 58 may be eliminated.

Figure 2:
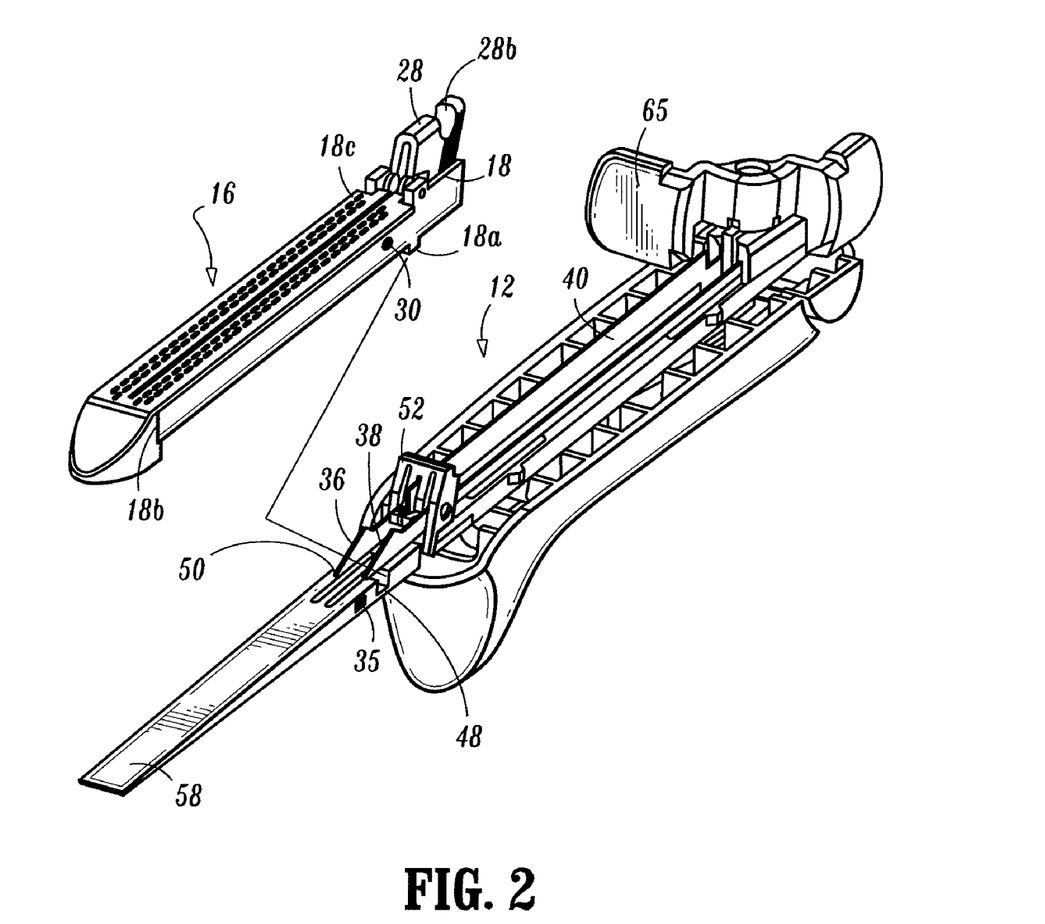
FIG. 2 is a perspective view with parts separated showing installation of the of the staple cartridge assembly of FIG. 1 on a cartridge half-section of the presently disclosed surgical fastener applying apparatus.

As shown in FIG. 2, a pair of camming surfaces 36, 38, which may be staggered, extend from a cam bar channel 40 to translate through the SULU 16 to expel pairs of staples (not shown) from the SULU 16. In addition, a knife blade may also translate along the length of the SULU 16 to bisect the tissue clamped between the cartridge receiving section 12 and the anvil section 14.

Figure 3:
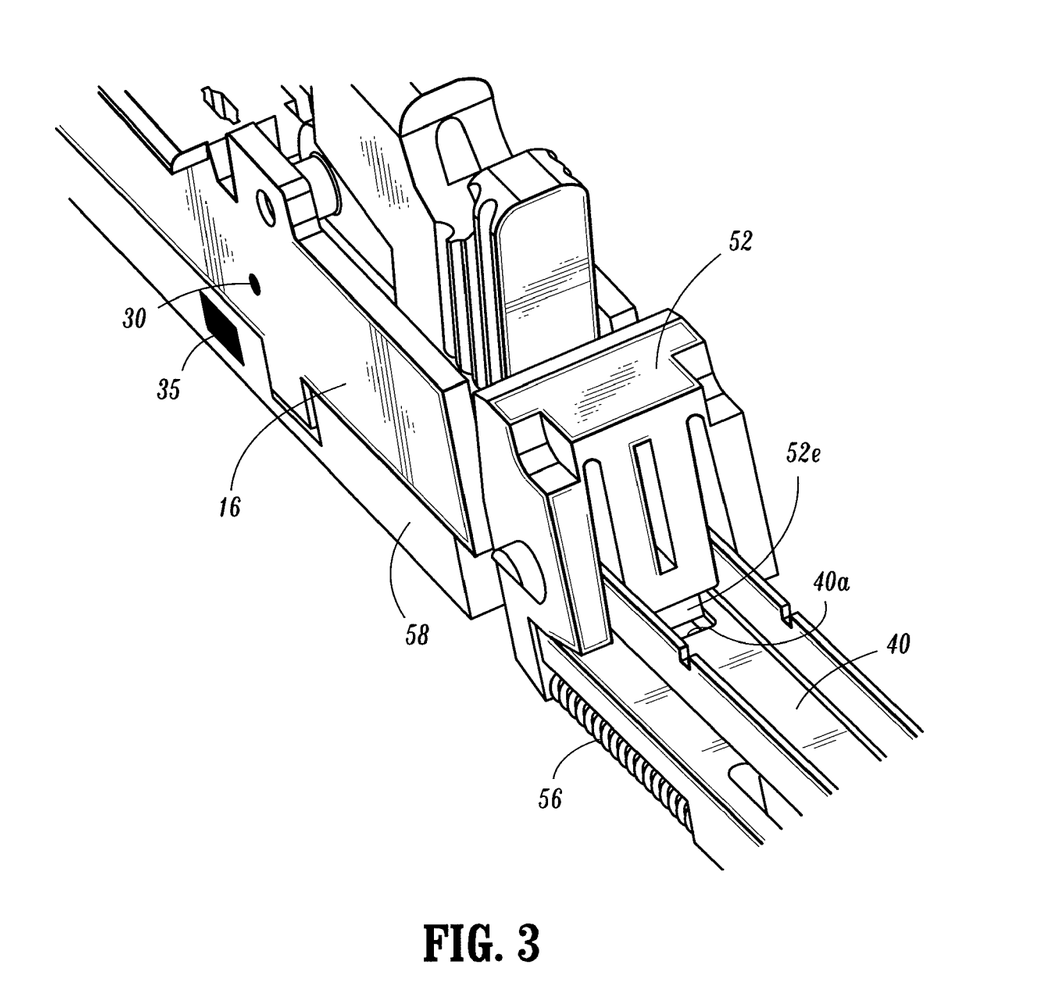
FIG. 3 is an enlarged right side proximal view of a staple cartridge loading and lockout mechanism with a staple cartridge in place.

As shown in FIGS. 2 and 3, a magnet 30 may be positioned on the SULU 16, and a sensor 35 may be positioned on the cartridge receiving section 12, e.g., at or near channel 40 or along the beam 58, in sufficient proximity to the magnet 30 to operatively interact with the magnet 30. The magnet 30 that is positioned on the SULU 16 is selected to have a measurable characteristic corresponding to a characteristic of the SULU 16 to be identified by the sensor 35.

Figure 4:
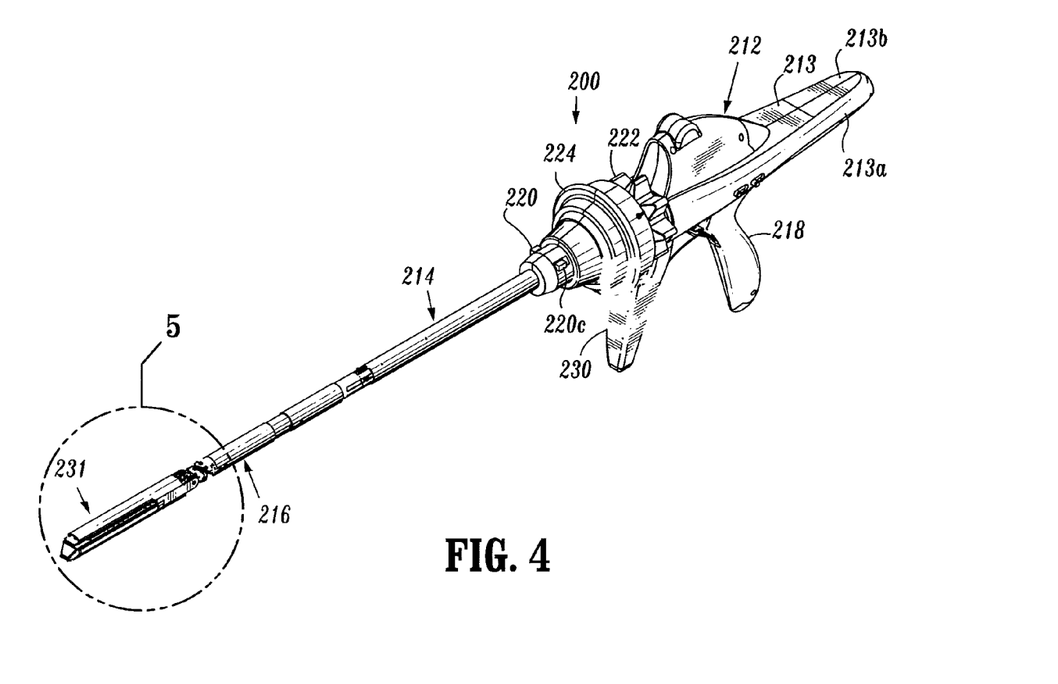
FIG. 4 is a side perspective view of another embodiment of a surgical stapling device including a cartridge assembly.

A surgical stapling device 200 will now be described with reference to FIGS. 4-5. The surgical stapling device 200 includes a proximal handle portion 212, an elongated central body portion 214, and an end effector 231. End effector 231 may optionally be detached from the elongated central body portion 214. In particular, distal shaft 216 may be detached, along with the end effector 231. The handle portion 212 includes a body 213 defining a stationary handle 218, a trigger 230, a rotation control member 222 for rotating and an articulation actuator 224. Body 213 includes a pair of molded half-sections 213a, 213b secured to each other using known fastening techniques, e.g., adhesives, welding, interlocking structure, screws, etc. Alternatively, other fastening techniques may be used. In addition, a locking mechanism to lock the end effector 231 in a particular position may be included. In particular, cut-outs 220 may engage protrusions 220c in a snap-fit relationship thereby releasably fixing the articulation actuator 224 and the rotation control member 222 in a particular position.

Figure 5:
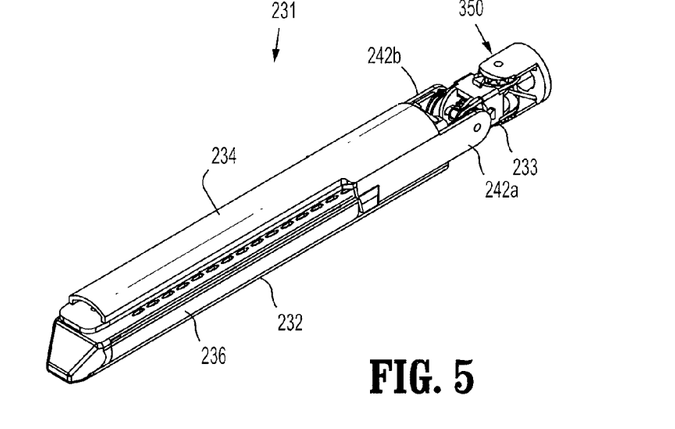
FIG. 5 is an enlarged view of the area indicated in FIG. 4 illustrating an end effector.
Figure 6:
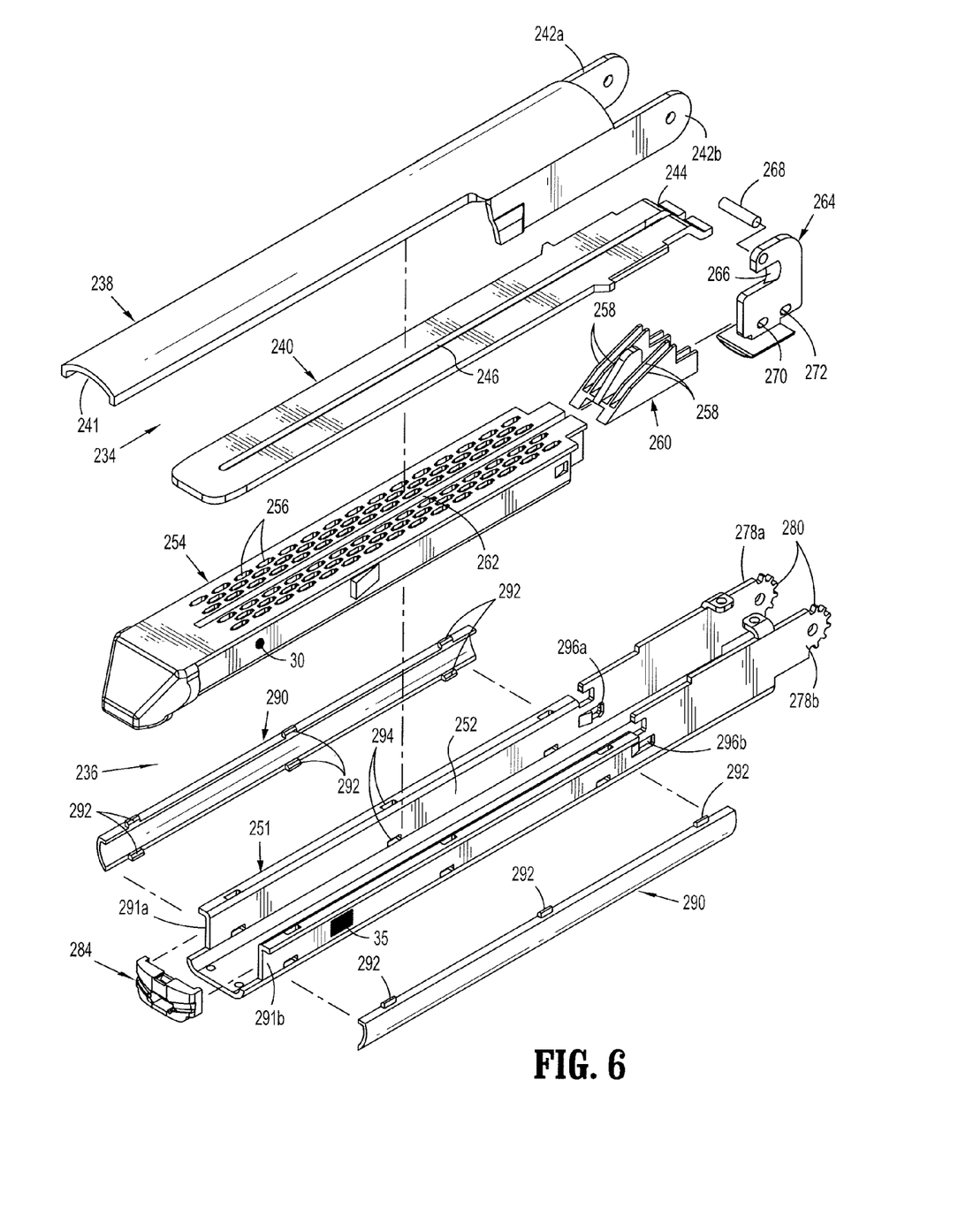
FIG. 6 is a view of the end effector of FIG. 5 with parts separated.

As shown in FIGS. 5 and 6, the end effector 231 includes an anvil assembly 234 and a cartridge assembly 236. The end effector 231 also includes a distal tool assembly 232 and an intermediate pivot member 233 that is operatively coupled to the distal tool assembly 232 at hinge members 242a, 242b. The anvil assembly 234 is configured and adapted to facilitate the formation of completed staples, as is known in the art, e.g., the anvil assembly 234 includes a plurality of staple deforming pockets.

In other embodiments, the end effector 231 may include a magnet 30 and the elongated central body portion 214 may include a sensor 35. Accordingly, in embodiments of the surgical stapling device 200 with interchangeable end effectors 231, recognition and identification of the end effector 231 may be facilitated. In addition, the end effector 231 may include a mounting member 350 that is adapted to be operatively connected to the distal shaft 216. The mounting member 350 may be adapted to facilitate pivoting of the end effector 231.

As shown best in FIG. 6, the end effector 231 includes an anvil body portion 238 and an anvil plate portion 240. The anvil plate portion 240 may include a plurality of staple deforming pockets (not shown), as is known in the art. The anvil plate portion 240 may be secured to the anvil body portion 238 using any known fastening technique, e.g., welding, crimping, etc. In an assembled condition, the anvil body portion 238 and anvil plate portion 240 define a gap or cavity 241 therebetween. The proximal end of the anvil body portion 238 includes the pair of hinge members 242a, 242b. The proximal portion of anvil plate 240 defines a cam surface 244. An elongated slot 246 extends from the proximal end of anvil plate portion 240 towards the distal end of the anvil plate portion 240.

Cartridge assembly 236 includes a carrier portion 251 defining an elongated support channel 252 dimensioned to receive a staple cartridge or SULU 254. Corresponding slots and grooves in the cartridge 254 and carrier portion 251 function to retain a cartridge, i.e., SULU 254. Corresponding slots and grooves in the SULU 254 and carrier portion 251 function to retain SULU 254 within support channel 252. The SULU 254 includes a plurality of staple slots or pockets 256 for receiving a plurality of fasteners, e.g., staples and pushers as is known in the art. An actuation sled 260 including can wedges 258 is configured and adapted to translate through the SULU to urge the pushers to eject staples through the slots or pockets 256. A knife bar 265 secured to the cam surface 244 by pin 268 includes a blade 266. The knife bar 265 is adapted to translate through slot 262. In addition, the knife bar may include holes 270, 272 that are configured and adapted to receive firing cables therethrough.

A carrier portion 251 includes a pair of hinge members 278a, 278b formed on a proximal end thereof, and may include serrations 280. A pivot pin may extend between hinge members 242a, 242b and hinge members 278a, 278b such that the anvil assembly 234 is pivotal in relation to cartridge assembly 236 between spaced and approximated positions relative to anvil body portion 238. A channel cover 290 may be secured to a side wall of the carrier portion 251 using tabs 292 that are received in slots 294. Channel covers 290 define cable channels, for example, 291a and 291b, for a firing cable along sidewalls of carrier portion 251. A pair of cutouts 296a and 296b are formed in carrier portion 251 to facilitate passage of a firing cable from channels 291a and 291b into cartridge support channel 252. A guide cap 284 or other suitable structure can be provided or secured to the distal end of carrier portion 250.

As shown in FIG. 6, a magnet 30 may be positioned on the SULU 254, and a sensor 35 may be positioned on the carrier portion 251, which receives SULU 254 and/or in sufficient proximity to the magnet 30 to operatively interact with the magnet 30. The magnet 30 that is positioned on the SULU 16 is selected to have a measurable characteristic corresponding to a characteristic of the SULU 16 to be identified by the sensor 35. In embodiments the magnet 30 may be operatively coupled to the end effector 231 and the sensor 35 may be operatively coupled to the elongated central body portion 214.

Figure 7:
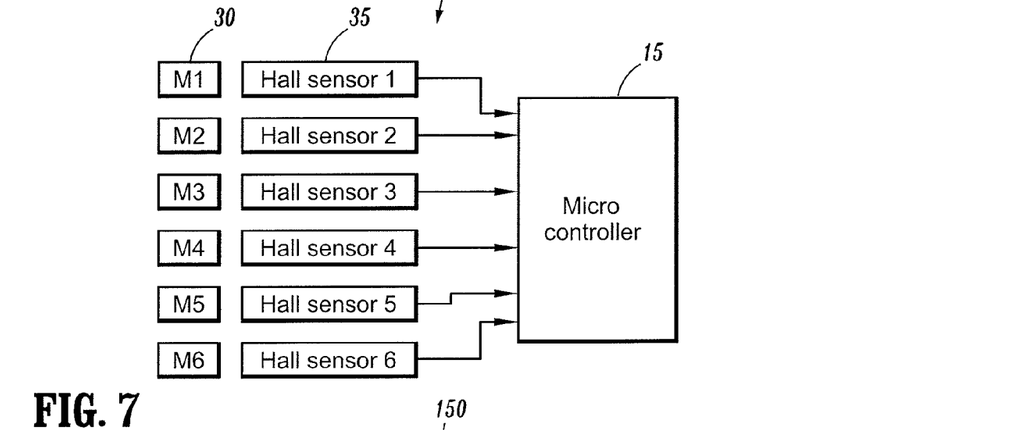
FIG. 7 is a block diagram of a component recognition system.
Figure 8:
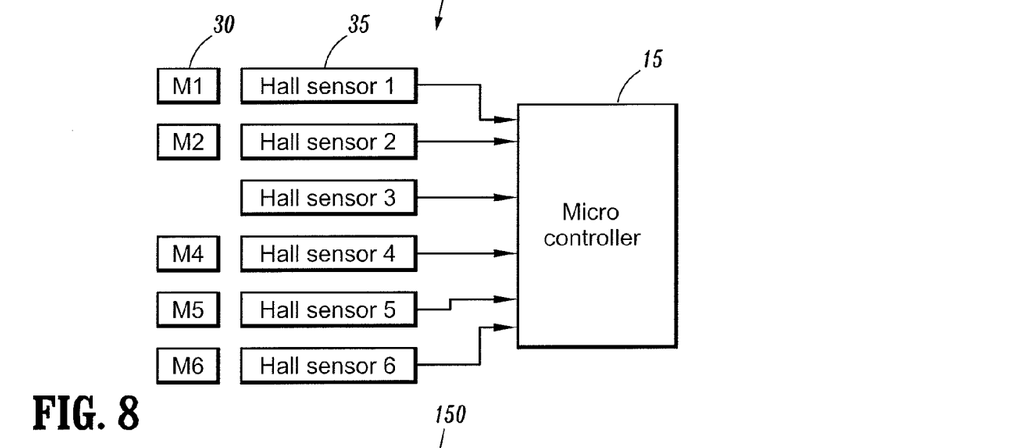
FIG. 8 is a block diagram of the component recognition system of FIG. 7 in a second state.
Figure 9:
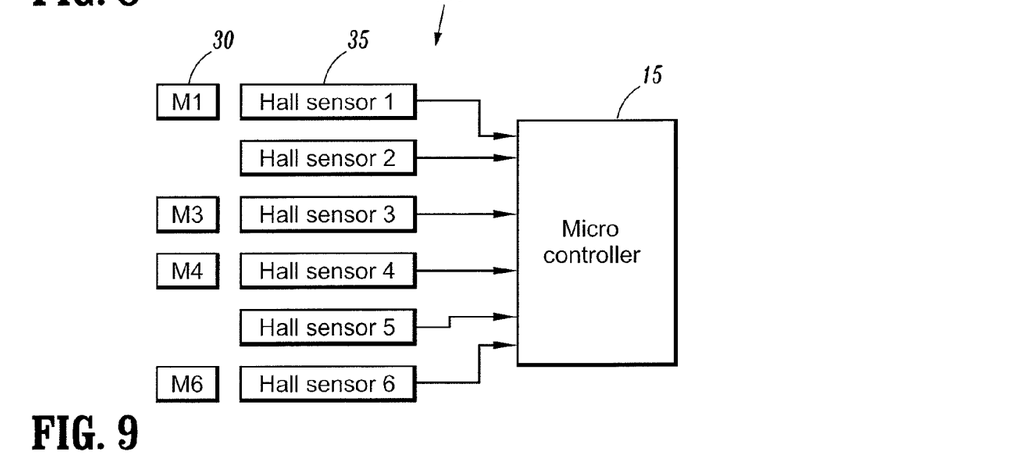
FIG. 9 is a block diagram of the component recognition system of FIG. 7 in a third state.

As shown in FIGS. 7-9, a component recognition system 150 includes a plurality of magnets 30. Each magnet 30 has a corresponding sensor 35, e.g., a hall-effect sensor. A hall-effect sensor is a transducer that varies its output in response to changes in the magnetic field. By detecting the changes in the proximity and/or strength of the magnets 30, the sensors 35 will be able to detect the presence and absence of the SULU 16, 254. In addition, the sensors 35 may detect particular characteristics of the magnets 30 that correspond with a particular SULU 16, 254 for identification and/or status purposes of the SULU 16, 254.

The magnets 30 are arranged on the SULU 16, 254 to represent a binary code, where each binary code corresponds to a characteristic of the SULU to be identified. The number of binary codes that can be created is a function of the number ("n") of sensors 35. In particular, the total number of binary codes is equal to two (2) raised to the "n" power, where n is equal to the total number of sensors. For example, if there are six (6) sensors 35, the total number of possible binary codes is sixty-four (64). Since the sensors 35 are capable of detecting not only the presence of a magnet, but also its strength, it is possible to represent more than 2 raised to the "n" power of characteristics by including magnets having different strengths. Accordingly, the number of combinations possible may be a function of the number of magnets as well as the strength of each individual magnet.

In each of FIGS. 7 to 9, six (6) sensors 35 are coupled to a microcontroller 15 that reads each signal to determine a binary code that corresponds with a characteristic to be identified. FIGS. 7 to 9 illustrate arrangements of magnets 30 in three different configurations. As seen in FIG. 7, each of the six (6) sensors 35 has a corresponding magnet 30 and therefore the binary code represented by this arrangement is equal to 111111. As shown in FIG. 8, a first sensor 35, a second sensor 35, a fourth sensor 35, a fifth sensor 35, and a sixth sensor 35 are each coupled to a different magnet 30, in that order. Such an arrangement corresponds to the binary code 110111. FIG. 9 illustrates yet another possible configuration of magnets 30 where a first sensor 35, a third sensor 35, a fourth sensor 35, and a sixth sensor 35 are each coupled to a different magnet 30, in that order. Such an arrangement corresponds to the binary code 101101.

Figure 10:
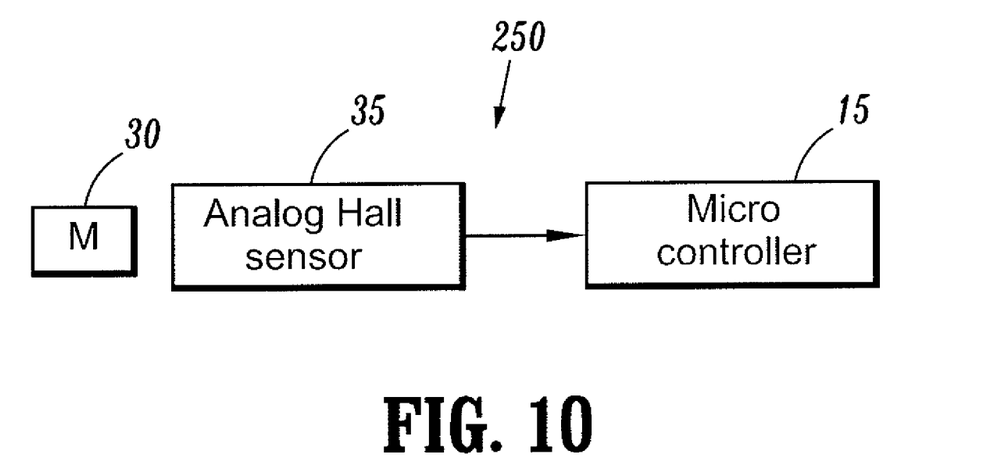
FIG. 10 is a block diagram of another embodiment of a component recognition system.

In yet another embodiment of a component recognition system 250, one sensor 35 is adapted to read the strength of one magnet 30. Each characteristic to be identified will correspond to a magnet 30 having a different magnetic strength, i.e., gauss power. To achieve this result, either different magnetic materials having different magnetic strengths or different amounts of the same material may be coupled to a component, e.g., SULU 16, 254, to correspond to the characteristic to be identified. The sensor 35 sends a signal to microcontroller 15 to identify the corresponding characteristic of the instrument.

Determination of the status of the SULU 16 may be achieved by moving or covering the magnets 30 as the SULU 16 is fired such that the number or strength of magnets 30 as measured by the sensor 20 may be dynamically altered. As such, various SULUs 16 may be provided with the surgical stapling device 10 and each SULU 16 has a configuration of magnets 30 that correspond to features of the particular SULU 16. The number of magnets 30 provided on a SULU 16 may indicate the number of rows of staples, the length of the SULU 16, the size of the staples provided in the SULU 16, as well as any other pertinent information that would facilitate selecting the correct SULU 16 for the surgical procedure to be performed. Further still, it is contemplated that the magnets 30 may be operatively coupled to movable magnetic components in the SULU 16 which would be detected by the sensors 20. In this instance, the component recognition system 10 would be capable of detecting whether or not the SULU 16 has jammed or has been previously used.

It will be understood by those skilled in the art that various modifications and changes in form and detail may be made herein without departing from the scope and spirit of the present disclosure. For example, a different arrangement, number, and position of the magnets 30 and sensors 35 that are included in surgical devices 10, 200 from that illustrated would remain within the scope and spirit of the present disclosure. Furthermore, the component recognition system described herein may be applied to any surgical instrument including interchangeable components where recognition of those components is desired. Accordingly, modifications and changes in form and detail may be made herein without departing from the scope and spirit of the present disclosure.

What is claimed is:

1. A surgical apparatus, comprising:
    a receiving section including one or more sensors; and
    an interchangeable component adapted and configured to be removably coupled to the receiving section, the interchangeable component including at least one magnet, the at least one magnet having an ordered arrangement representing a binary code corresponding to a characteristic of the interchangeable component, the at least one magnet being detectable by the one or more sensor, wherein the at least one magnet is movable relative to the one or more sensor, whereby strength and detectability of the at least one magnet is dynamically alterable in response to a change in status of the surgical apparatus.

2. The surgical apparatus of claim 1, wherein the at least one sensor includes a number of sensors, each sensor being adapted and configured to detect a magnet, the interchangeable component having a number of magnets, the number of magnets being equal or fewer than the number of sensors, the magnets being arranged to interact with particular sensors such that particular sensors will detect a presence of a magnet.

3. The surgical apparatus of claim 1, wherein the at least one sensor includes a number of sensors, each sensor being adapted and configured to detect a magnet, the interchangeable component having a number of magnets, the number of magnets being equal or fewer than the number of sensors, the magnets being arranged to interact with particular sensors such that particular sensors will detect an absence of a magnet.

4. The surgical apparatus of claim 1, wherein the receiving section is a cartridge receiving section and the interchangeable component is a loading unit adapted and configured to be received by the cartridge receiving section.

5. The surgical apparatus of claim 4, wherein the loading unit is a staple cartridge and the characteristic of the interchangeable component is a size or a dimension of one or more staples contained within the staple cartridge.

6. The surgical apparatus of claim 1, wherein the receiving section is an elongated body portion and the interchangeable component is an end effector, the elongated body portion and the end effector being adapted and configured to be operatively coupled to each other.

7. The surgical apparatus of claim 1, wherein the at least one sensor is a hall-effect sensor.

8. The surgical apparatus of claim 1, wherein the change in status corresponds to actuation of the surgical apparatus.

9. The surgical apparatus of claim 1, wherein the change in status corresponds to firing of a staple cartridge.

* * * * *